(12) United States Patent
Hirota et al.

(10) Patent No.: US 8,937,200 B2
(45) Date of Patent: Jan. 20, 2015

(54) METHOD FOR PRODUCING 2-(ARYLOXYMETHYL) BENZALDEHYDE COMPOUND

(75) Inventors: Masaji Hirota, Osaka (JP); Masashi Takimoto, Shizuoka (JP); Tomonori Yamaoka, Shizuoka (JP); Yoshio Onogawa, Shizuoka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 14/129,186

(22) PCT Filed: Jun. 27, 2012

(86) PCT No.: PCT/JP2012/066403
§ 371 (c)(1),
(2), (4) Date: Mar. 19, 2014

(87) PCT Pub. No.: WO2013/002266
PCT Pub. Date: Jan. 3, 2013

(65) Prior Publication Data
US 2014/0221695 A1 Aug. 7, 2014

(30) Foreign Application Priority Data
Jun. 29, 2011 (JP) .................................. 2011-143888

(51) Int. Cl.
*C07C 45/43* (2006.01)

(52) U.S. Cl.
CPC ....................................... *C07C 45/43* (2013.01)
USPC .......................................................... 568/437

(58) Field of Classification Search
CPC ........................................................ C07C 45/43
USPC ........................................................ 568/437
See application file for complete search history.

(56) References Cited

U.S. PATENT DOCUMENTS

| | | | |
|---|---|---|---|
| 7,851,659 B2 | 12/2010 | Nakazawa | |
| 7,994,367 B2 | 8/2011 | Nakazawa | |
| 8,258,349 B2 | 9/2012 | Nakazawa | |
| 8,338,625 B2 | 12/2012 | Onogawa et al. | |
| 2006/0293542 A1 | 12/2006 | Giselbrecht et al. | |
| 2010/0210879 A1 | 8/2010 | Nakazawa | |
| 2010/0234645 A1 | 9/2010 | Nakazawa | |
| 2010/0292513 A1 | 11/2010 | Nakazawa | |
| 2011/0098489 A1 | 4/2011 | Onogawa et al. | |

FOREIGN PATENT DOCUMENTS

| | | |
|---|---|---|
| CN | 1626493 A | 6/2005 |
| CN | 1891680 A | 1/2007 |
| CN | 101939281 A | 1/2011 |
| JP | 09-095462 A | 4/1997 |
| JP | 09-124538 A1 | 5/1997 |
| JP | 2006-335737 A1 | 12/2006 |
| JP | 2009-1554 A | 1/2009 |
| JP | 2009-7334 A | 1/2009 |
| JP | 2009-215286 A | 9/2009 |
| JP | 2009-298746 A | 12/2009 |
| WO | 2009/101898 A1 | 8/2009 |

OTHER PUBLICATIONS

International Preliminary Report on Patentability issued Jan. 7, 2014 in International Application No. PCT/JP2012/066403.
First Office Action issued Sep. 25, 2014 in counterpart Chinese Patent Application No. 201280031618.3 with English translation.

*Primary Examiner* — Sikarl Witherspoon
(74) *Attorney, Agent, or Firm* — Sughrue Mion, PLLC

(57) ABSTRACT

A new process capable of producing a 2-(aryloxymethyl) benzaldehyde compound is provided. More particularly, a process for producing a 2-(aryloxymethyl)benzaldehyde compound represented by formula (2) comprising a step of hydrolyzing a compound represented by following formula (1);

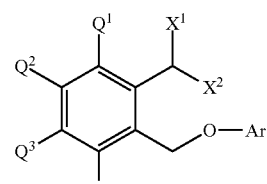

(1)

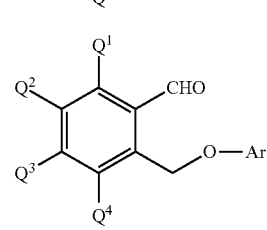

(2)

wherein $X^1$ and $X^2$ each represent independently a chlorine atom, a bromine atom or an iodine atom, $Q^1$, $Q^2$, $Q^3$ and $Q^4$ each represent independently a hydrogen atom or a halogen atom, and Ar represents a phenyl group optionally having a substituent.

3 Claims, No Drawings

METHOD FOR PRODUCING 2-(ARYLOXYMETHYL) BENZALDEHYDE COMPOUND

This application is a National Stage of International Application No. PCT/JP2012/066403, filed Jun. 27, 2012, claiming priority based on Japanese Patent Application No. 2011-143888, filed Jun. 29, 2011, the contents of all of which are incorporated herein by reference in their entirely.

TECHNICAL FIELD

The present invention relates to a process for producing a 2-(aryloxymethyl)benzaldehyde compound.

BACKGROUND ART

A 2-(aryloxymethyl)benzaldehyde compound such as 2-(2,5-dimethylphenoxymethyl)benzaldehyde has been known to be useful, for example, as an intermediate for producing agricultural germicides (for example, see JP 9-95462 A).

As a process for producing 2-(aryloxymethyl)benzaldehyde, for example, the following method is described in JP 2009-215286 A (Example 5). In the method, 2-(2,5-dimethylphenoxymethyl)benzaldehyde is obtained by reacting 2-(2,5-dimethylphenoxymethyl)benzal chloride and sodium methoxide, and then a resulting acetal compound is extracted with xylene. Then, an organic layer obtained after liquid separation is mixed with an aqueous sulfuric acid solution to hydrolyze the acetal compound to obtain 2-(2,5-dimethylphenoxymethyl)benzaldehyde.

An object of the present invention is to provide a new process capable of producing a 2-(aryloxymethyl)benzaldehyde compound.

SUMMARY OF INVENTION

The present inventors intensively studied, and reached the present invention.

That is, the present invention is as follows:

[1] A process for producing a 2-(aryloxymethyl)benzaldehyde compound represented by formula (2):

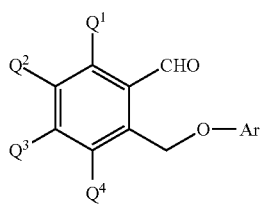

(2)

wherein $Q^1$, $Q^2$, $Q^3$ and $Q^4$ each represent independently a hydrogen atom or a halogen atom, and Ar represents a phenyl group optionally having a substituent, the process comprising a step of hydrolyzing a compound represented by formula (1):

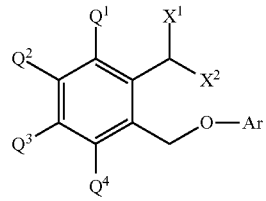

(1)

wherein $X^1$ and $X^2$ each represent independently a chlorine atom, a bromine atom or an iodine atom, and $Q^1$, $Q^2$, $Q^3$, $Q^4$ and Ar are each as described above, in the presence of an organic acid and a salt of an organic acid.

[2] The process according to [1], wherein the step is a step of hydrolyzing the compound represented by formula (1) further in the presence of a phase transfer catalyst.

[3] The process according to [1] or [2], wherein the organic acid is a carboxylic acid having 2 to 6 carbon atoms and the salt of an organic acid is an alkali metal salt of a carboxylic acid having 2 to 6 carbon atoms.

According to the present invention, a new process capable of producing a 2-(aryloxymethyl)benzaldehyde compound can be provided.

DESCRIPTION OF EMBODIMENT

The present invention will be explained in detail below.

In formula (1), $X^1$ and $X^2$ each represent independently a chlorine atom, a bromine atom or an iodine atom. $X^1$ and $X^2$ are preferably the same atom, and more preferably both of them are a chlorine atom from the viewpoint of economical efficiency.

In formulae (1) and (2), $Q^1$, $Q^2$, $Q^3$ and $Q^4$ each represent independently a hydrogen atom or a halogen atom. Examples of the halogen atom represented by $Q^1$, $Q^2$, $Q^3$ and $Q^4$ include a fluorine atom, a chlorine atom, a bromine atom and an iodine atom. $Q^1$, $Q^2$, $Q^3$ and $Q^4$ are preferably a hydrogen atom.

In formulae (1) and (2), Ar represents a phenyl group optionally having a substituent.

Examples of the substituent that the phenyl group has include, an alkyl group having 1 to 4 carbon atoms such as a methyl group, an ethyl group, a propyl group, an isopropyl group, a butyl group, an isobutyl group and a tert-butyl group; and a halogen atom such as a fluorine atom and a chlorine atom. When the phenyl group has the substituent, the number of the substituent is not limited, and is preferably 1 to 3, more preferably 1 or 2, and most preferably 2.

Examples of the phenyl group optionally having a substituent represented by Ar include, for example, a phenyl group, a 2-methylphenyl group, a 3-methylphenyl group, a 4-methylphenyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, a 2,4,6-trimethylphenyl group, a 2-ethylphenyl group, a 3-ethylphenyl group, a 4-ethylphenyl group, a 2,3-diethylphenyl group, a 2,4-diethylphenyl group, a 2,5-diethylphenyl group, a 2,6-diethylphenyl group, a 3,5-diethylphenyl group, a 2,4,6-triethylphenyl group, a 2-(n-propyl)phenyl group, a 3-(n-propyl)phenyl group, a 4-(n-propyl)phenyl group, a 2,4-di(n-propyl)phenyl group, a 2,5-di(n-propyl)phenyl group, a 2,6-di(n-propyl)phenyl group, a 2,4,6-tri(n-propyl)phenyl group, a 2-isopropylphenyl group, a 3-isopropylphenyl group, a 4-isopropylphenyl group, a 2,4-diisopropylphenyl group, a 2,5-diisopropylphenyl group, a 2,6-diisopropylphenyl group, a 2,4,6-triisopropylphenyl group, a 2-(n-butyl)phenyl group, a 3-(n-butyl)phenyl group, a 4-(n-butyl)phenyl group, a 2,4-di(n-butyl)phenyl group, a 2,5-di(n-butyl)phenyl group, a 2,6-di(n-butyl)phenyl group, a 2,4,6-tri(n-butyl)phenyl group, a 2-isobutylphenyl group, a 3-isobutylphenyl group, a 4-isobutylphenyl group, a 2,4-diisobutylphenyl group, a 2,5-diisobutylphenyl group, a 2,6-diisobutylphenyl group, a 2,4,6-triisobutylphenyl group, a 2-(tert-butyl)phenyl group, a 3-(tert-butyl)phenyl group, a 4-(tert-butyl)phenyl group, a 2,5-di-(tert-butyl)phenyl group, a 2,4-di-(tert-butyl)phenyl group, a 2,6-di-(tert-butyl)phenyl group, a 2,4,6-tri-(tert-butyl)phenyl group, a 2-fluorophenyl group, a 4-fluorophenyl group, a 2,4-difluorophenyl group, a 2,4,6-trifluorophenyl group, a pentafluorophenyl group, a 2-chlorophenyl group, a 4-chlorophenyl group, a 2,4-dichlorophenyl group, a 2,4,6-trichlorophenyl group and a pentachlorophenyl group.

The phenyl group optionally having a substituent represented by Ar is preferably a phenyl group, a 2-methylphenyl group or a 2,5-dimethylphenyl group, more preferably a 2-methylphenyl group or a 2,5-dimethylphenyl group, and most preferably a 2,5-dimethylphenyl group.

The process of the present invention comprises a step of hydrolyzing a compound represented by formula (1) (hereinafter, referred to as "compound (1)" in some cases) in the presence of an organic acid and a salt of an organic acid. Hereinafter, the step of hydrolyzing the compound (1) in the presence of an organic acid and a salt of an organic acid is referred to as "present reaction" in some cases. According to the present reaction, the compound (1) is converted to a 2-(aryloxymethyl)benzaldehyde compound represented by formula (2) (hereinafter, referred to as "compound (2)" in some cases).

Examples of the compound (1) used in the present reaction include, for example, 2-(phenoxymethyl)benzal chloride, 2-(2-ethylphenoxymethyl)benzal chloride, 2-(2-ethylphenoxymethyl)benzal chloride, 2-(2-isopropylphenoxymethyl) benzal chloride, 2-(4-methylphenoxymethyl)benzal chloride, 2-(4-isopropylphenoxymethyl)benzal chloride, 2-(2,5-dimethylphenoxymethyl)benzal chloride, 2-(2,5-diethylphenoxymethyl)benzal chloride, 2-(2,5-diisopropylphenoxymethyl)benzal chloride, 2-(2,4,5-trimethylphenoxymethyl)benzal chloride, 2-(2,4,6-trimethylphenoxymethyl)benzal chloride, 2-(3,4,5-trimethylphenoxymethyl)benzal chloride, 2-(2,5-dimethylphenoxymethyl)-3-chlorobenzal chloride, 2-(2,5-dimethylphenoxymethyl)-4-chlorobenzal chloride, 2-(2,5-dimethylphenoxymethyl)-5-chlorobenzal chloride, 2-(2,5-dimethylphenoxymethyl)-6-chlorobenzal chloride, 2-(2,5-diethylphenoxymethyl)-3-chlorobenzal chloride, 2-(2,5-diethylphenoxymethyl)-4-chlorobenzal chloride, 2-(2,5-diethylphenoxymethyl)-5-chlorobenzal chloride, 2-(2,5-diethylphenoxymethyl)-6-chlorobenzal chloride, 2-(2,5-diisopropylphenoxymethyl)-3-chlorobenzal chloride, 2-(2,5-diisopropylphenoxymethyl)-4-chlorobenzal chloride, 2-(2,5-diisopropylphenoxymethyl)-5-chlorobenzal chloride, 2-(2,5-diisopropylphenoxymethyl)-6-chlorobenzal chloride, 2-(2,5-dimethylphenoxymethyl)benzal bromide, 2-(2,5-dimethylphenoxymethyl)benzal iodide, 2-(2,5-dimethylphenoxymethyl)-4-bromobenzal bromide, 2-(2,5-diethylphenoxymethyl)-4-bromobenzal bromide, 2-(2,5-diisopropylphenoxymethyl)-4-bromobenzal bromide and 2-(2,5-dimethylphenoxymethyl)-4-iodobenzal iodide.

The compound (1) is preferably 2-(2,5-dimethylphenoxymethyl)benzal chloride.

The compound (1) may be produced, for example, by reacting a compound represented by formula (3):

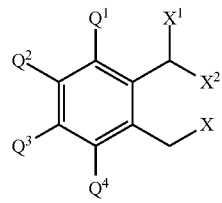

wherein $X^1$, $X^2$, $Q^1$, $Q^2$, $Q^3$ and $Q^4$ are each as described above, and X represents a chlorine atom, a bromine atom or a iodine atom, (hereinafter, referred to as "compound 3" in some cases) and a compound represented by formula (4):

HO—Ar                                                      (4)

wherein Ar is as described above, in the presence of a base.

Examples of the compound (3) used in production of the compound (1) include, for example, 2-(chloromethyl)benzal chloride, 2-(bromomethyl)benzal bromide, 2-(iodomethyl) benzal iodide, 3-chloro-2-(chloromethyl)benzal chloride, 4-chloro-2-(chloromethyl)benzal chloride, 4-bromo-(bromomethyl)benzal bromide, 4-iodo-2-(iodomethyl)benzal iodide, 5-chloro-2-(chloromethyl)benzal chloride, 5-bromo-(bromomethyl)benzal bromide, 5-iodo-2-(iodomethyl)benzal iodide and 6-chloro-2-(chloromethyl)benzal chloride. Preferably, the compound (3) is 2-(chloromethyl)benzal chloride from the viewpoint of its availability. The compound (3) may be a compound which is commercially available or, for example, a compound produced according to a method in which an ortho-xylene compound is reacted with halogen in the presence of a radical initiator or under light radiation (for example, see JP 2006-335737 A).

Examples of the compound (4) used in production of the compound (1) include, for example, phenol, 2-methylphenol, 2-ethylphenol, 2-isopropylphenol, 4-methylphenol, 4-isopropylphenol, 2,5-dimethylphenol, 2,5-diethylphenol, 2,5-diisopropylphenol, 2,4,5-trimethylphenol, 2,4,6-trimethylphenol, 3,4,5-trimethylphenol, 2-chlorophenol, 4-chlorophenol, 2-fluorophenol, 4-fluorophenol, 2,4-difluorophenol and 2,4,6-trifluorophenol. Among them, 2,5-dimethylphenol is preferable. The compound (4) may be a compound which is commercially available, or may be a compound produced by the method described, for example, in J. Am. Chem. Soc., 128, 10694 (2006), Tetrahedron Letters, 30, 5215 (1989), JP 2002-3426 A or the like.

A use amount of the compound (3) and the compound (4) is not particularly limited, and 10 mol or more of either of compounds may be used based on 1 mol of another compound.

A use amount of the compound (4) is, for example, in the range of 0.1 mol to 10 mol, and preferably in the range of 1 mol to 3 mol based on 1 mol of the compound (3).

Examples of the base used in production of the compound (1) include, for example, tertiary amines such as trimethylamine, triethylamine and diisopropylethylamine; metal alkoxides such as sodium methoxide, sodium ethoxide and potassium tert-butoxide; alkali metal hydroxides such as lithium hydroxide, sodium hydroxide and potassium hydroxide; alkaline metal hydrides such as sodium hydride, potassium hydride and lithium hydride; alkali metal carbonate compounds such as sodium carbonate, potassium carbonate and lithium carbonate; alkali metal bicarbonate compounds such as sodium bicarbonate, potassium bicarbonate and lithium bicarbonate, and the like. The base is preferably alkali metal hydroxide, and more preferably sodium hydroxide. As such a base, a base which is commercially available may be used as it is, or the base may be used after it is mixed with water or a solvent described later or is concentrated. A use amount of the base is, for example, 1 mol or more, preferably in the range of 1 to 3 mol based on 1 mol of either smaller use amount compound of the compound (3) and the compound (4).

A reaction of the compound (3) and the compound (4) may be carried out in the presence of a solvent. Examples of such a solvent include, for example, aromatic solvents such as xylene, toluene and benzene; aliphatic hydrocarbon solvents such as pentane, hexane, heptane and cyclohexane; ether solvents such as tetrahydrofuran, diethyl ether, tert-butylmethyl ether and cyclopentylmethyl ether; nitrile solvents such as acetonitrile and propionitrile; ketone solvents such as tert-buthyl methyl ketone; amide solvents such as N,N-dimethylformamide; sulfoxide solvents such as dimethylsulfoxide; water; and the like. These solvents may be alone, or may be a mixture of two or more kinds. The solvent is preferably water and an aromatic solvent, and more preferably water and toluene. A use amount of the solvent is not particularly limited, but it is, for example, 100 parts by weight or less based on 1 part by weight of the compound (3) from the viewpoint of economical efficiency.

A reaction of the compound (3) and the compound (4) is carried out preferably in the presence of a phase transfer catalyst. Examples of such a phase transfer catalyst include quaternary ammonium salts such as tetra-n-butylammonium bromide, benzyltriethylammonium chloride, tetra-n-butylammonium hydrogen sulfate, trioctylmethylammonium chloride; phosphonium salts such as triphenylphosphine bromide; and polyether compounds such as 18-crown-6 and polyethylene glycol, and the like. Among them, the phase transfer catalyst is preferably a quaternary ammonium salt, and more preferably tetra-n-butylammonium bromide. A use amount of the phase transfer catalyst is, for example, 0.10 mol or more, and preferably in the range of 0.05 mol to 1 mol based on 1 mol of an either smaller amount compound of the compound (3) and the compound (4).

A reaction of the compound (3) and the compound (4) may progress smoothly in the presence of an iodine compound. Examples of such an iodine compound include, for example, alkali metal iodides such as potassium iodide, sodium iodide and lithium iodide, iodine, and the like. The iodine compound is preferably alkali metal iodide, and more preferably potassium iodide. The iodine compound may be, for example, an iodine compound which is commercially available, or may be an iodine compound produced by the arbitrary known method. A use amount of the iodide compound is, for example, 0.01 mol or more, and preferably in the range of 0.05 mol to 1 mol based on 1 mol of a either smaller amount compound of the compound (3) and the compound (4).

The reaction temperature in the reaction of the compound (3) and the compound (4) is selected, for example, from the range of −5° C. to a boiling point of the solvent, and preferably selected from the range of 10° C. to 100° C., and more preferably from the range of 50° C. to 90° C. Such a reaction may be carried out under atmospheric pressure, or may be carried out under pressure. The degree of progression of such a reaction can be confirmed by the analysis means such as gas chromatography, high-performance liquid chromatography and NMR.

The reaction of the compound (3) and the compound (4) may be carried out by mixing the compound (3) and the compound (4) with a base, and a mixing order of them is not particularly limited. For example, there are methods in which, after mixing the compound (3), the compound (4) and the base, the resulting mixture is adjusted to the predetermined reaction temperature; the compound (3), the compound (4) and the base are mixed under the predetermined reaction temperature condition; the base is added to a mixture of the compound (3) and the compound (4) which has been adjusted to the predetermined reaction temperature; the compound (4) is added to a mixture of the compound (3) and the base which has been adjusted to the predetermined reaction temperature; a mixture of the compound (4) and the base which has been adjusted to the predetermined reaction temperature is added to the compound (3), and the like. Among them, the method in which a mixture of the compound (4) and the base which has been adjusted to the predetermined reaction temperature is added to the compound (3) is preferable.

After the reaction of the compound (3) and the compound (4), the compound (1) can be obtained. The compound (1) may be subjected to the present reaction as it is, or may be subjected to the present reaction after post-treatment. Examples of such post-treatment include, for example, neutralization treatment, liquid separation treatment, and the like. A mixture obtained by post-treatment may be subjected to the present reaction as it is or, for example, may be subjected to the present reaction after separation of the compound (1) by the means such as concentration, crystallization and filtration. Moreover, the separated compound (1) may be subjected to the present reaction after purification by the purification means such as recrystallization, distillation and column chromatography.

Examples of the organic acid used in the present reaction include, for example, an organic sulfonic acid and an carboxylic acid. Examples of the organic sulfonic acid include, for example, aliphatic organic sulfonic acids such as methanesulfonic acid, ethanesulfonic acid and trifluoromethanesulfonic acid; as well as aromatic sulphonic acids such as benzenesulfonic acid and toluenesulfonic acid. Examples of the carboxylic acid include aliphatic carboxylic acids such as methanoic acid (formic acid), ethanoic acid (acetic acid), propanoic acid (propionic acid), butanoic acid (butyric acid), pentanoic acid (valeric acid), hexanoic acid (caproic acid), heptanoic acid (enanthic acid) and octanoic acid (caprylic acid); and aromatic carboxylic acids such as benzene carboxylic acid (benzoic acid). The organic acid is preferably a carboxylic acid, more preferably a carboxylic acid having 2 to 6 carbon atoms, and most preferably acetic acid. A use amount of the organic acid is preferably in the range of 1 to 20 mol, and more preferably in the range of 5 to 10 mol based on 1 mol of the compound (1).

Examples of the organic acid used in the present reaction include, for example, alkali metal salts of an organic sulfonic acid, alkaline earth metal salts of an organic sulfonic acid, alkali metal salts of a carboxylic acid and alkaline earth metal salts of a carboxylic acid. Examples of the alkali metal salts of an organic sulfonic acid include, for example, a lithium salt of the organic sulfonic acid as described above, a sodium salt of the organic sulfonic acid as described above and a potassium salt of the organic sulfonic acid as described above. Examples of the alkaline earth metal salts of an organic sulfonic acid include, for example, a calcium salt of the organic sulfonic acid as described above and a magnesium salt of the organic sulfonic acid as described above. Examples of the alkali metal salts of a carboxylic acid include, for example, a lithium salt of the carboxylic acid as described above, a sodium salt of the carboxylic acid as described above, a potassium salt of the carboxylic acid as described above and a cesium salt of the carboxylic acid as described above. The salt of an organic acid is preferably at least one selected from the group consisting of an alkali metal salt of a carboxylic acid and an alkaline earth metal salt of a carboxylic acid, more preferably an alkali metal salt of a carboxylic acid having 2 to 6 carbon atoms, and most preferably an alkali metal salt of acetic acid. The salt of an organic acid salt may be one commercially available, or one prepared from an organic acid and a base. Examples of such a base include, for example, alkali metal hydroxides such as lithium hydroxide, sodium hydroxide, potassium hydroxide and cesium hydroxide; alkali metal carbonates such as lithium carbonate, lithium hydrogencarbonate, sodium carbonate, sodium hydrogencarbonate, potassium carbonate, potassium hydrogencarbonate, cesium carbonate and cesium hydrogencarbonate; alkaline earth metal hydroxides such as calcium hydroxide and magnesium hydroxide; and alkaline earth metal salts such as calcium carbonate and magnesium carbonate. A use amount of the salt of an organic acid is preferably in the range of 1 to 10 mol, and more preferably in the range of 1 to 5 mol based on 1 mol of the compound (1).

The present reaction is carried out in the presence of water. A use amount of water is preferably 1 mol or more based on 1 mol of the compound (1), but an upper limit thereof is not restricted. A use amount of water is more preferably in the range of 1 to 5 mol based on 1 mol of the compound (1). When a use amount of water is less than 1 mol based on 1 mol of the compound (1), a yield of the compound (1) tends to decrease.

The present reaction may be carried out in the absence of the organic solvent or in the presence of the organic solvent, but the present reaction is preferably carried out in the absence of the organic solvent. In the case where the present reaction is carried out in the presence of the organic solvent, examples of such an organic solvent include, for example, aromatic solvents such as xylene, toluene and benzene; aliphatic hydrocarbon solvents such as pentane, hexane, heptane and cyclohexane; ether solvents such as tetrahydrofuran, diethyl ether, tert-butylmethyl ether and cyclopentylmethyl ether; nitrile solvents such as acetonitrile and propionitrile; ketone solvents such as tert-butyl methyl ketone; amide solvents such as N,N-dimethylformamide; sulfoxide solvents such as dimethylsulfoxide, and the like. These solvents may be alone, or may be a mixture of two or more kinds. In the case where the organic solvent is used, a use amount thereof is not particularly limited, but it is, for example, 100 parts by weight or less based on 1 part by weight of the compound (3) from the viewpoint of improved volume efficiency of the present reaction.

The present reaction is carried out preferably in the presence of a phase transfer catalyst. Examples of such a phase transfer catalyst include quaternary ammonium salts such as tetra-n-butylammonium bromide, benzyltriethylammonium chloride, tetra-n-butylammonium hydrogen sulfate and trioctylmethylammonium chloride; phosphonium salts such as triphenylphosphine bromide; and polyether compounds such as 18-crown-6 and polyethylene glycol. The phase transfer catalyst is preferably a quaternary ammonium salt, and more preferably tetra-n-butylammonium bromide. A use amount of the phase transfer catalyst is, for example, 0.001 mol or more, preferably in the range of 0.001 mol to 0.1 mol, and most preferably in the range of 0.001 mol to 0.05 mol based on 1 mol of the compound (1).

The reaction temperature of the present reaction is selected from, for example, the range of 40 to 150° C., preferably from the range of 100 to 140° C. The present reaction may be carried out under atmospheric pressure, under pressure, or reduced pressure.

The present reaction may be carried out by mixing the compound (I), the organic acid, the salt of an organic acid, water and, if necessary, the phase transfer catalyst, and, if necessary, the organic solvent at the predetermined reaction temperature. A mixing order is not limited. Specifically, the present reaction may be carried out, for example, by mixing the organic acid, the salt of an organic acid, water and, if necessary, the phase transfer catalyst, and, if necessary, the organic solvent and adjusting the mixture to the predetermined reaction temperature, by mixing the organic acid, an salt of organic acid, water and, if necessary, the phase transfer catalyst, and, if necessary, the organic solvent and adjusting the mixture to the predetermined temperature, then adding the compound (1), if necessary, diluted with the organic solvent, thereto, or by mixing the compound (1), the salt of organic acid, water and, if necessary, the phase transfer catalyst, and, if necessary, the organic solvent, adjusting the mixture to the predetermined temperature, and then adding the organic acid, if necessary, diluted with an organic solvent, to the mixture. In addition, the present reaction may be carried out by mixing the compound (1), water and, if necessary, the organic solvent, and then adding the organic acid, if necessary, diluted with the organic solvent, to the mixture. In addition, the present reaction may be carried out by mixing the compound (1), water, if necessary, the phase transfer catalyst and, if necessary, the organic solvent, adjusting the mixture to the predetermined temperature, and adding a mixture of the organic acid and the salt of organic acid, if necessary diluted with the organic solvent, to the mixture, or by mixing the compound (1), the organic acid, the salt of organic acid, if necessary, the phase transfer catalyst and, if necessary, the organic solvent, adjusting the mixture to the predetermined temperature, and adding water to the mixture.

The degree of progression of the present reaction can be confirmed by the analysis means such as gas chromatography, high-performance liquid chromatography and NMR.

After the present reaction, the compound (1) is hydrolyzed to obtain the compound (2). The compound (2) obtained after the present reaction can be separated, for example, by, if necessary, mixing it with a water-immiscible organic solvent, if necessary, subjecting to neutralization treatment, and conducting liquid separation and concentration treatment, and the like. Examples of the water-immiscible organic solvent include, for example, aromatic solvents such as xylene, toluene and benzene; aliphatic hydrocarbon solvents such as pentane, hexane, heptane and cyclohexane; and ester solvents such as methyl acetate and ethyl acetate. The compound (2) separated can be purified by the purification means such as distillation, recrystallization and column chromatography.

Examples of the compound (2) thus obtained include 2-(phenoxymethyl)benzaldehyde, 2-(2-methylphenoxymethyl)benzaldehyde, 2-(2-ethylphenoxymethyl)benzaldehyde, 2-(2-isopropylphenoxymethyl)benzaldehyde, 2-(4-methylphenoxymethyl)benzaldehyde, 2-(4-isopropylphenoxymethyl)benzaldehyde, 2-(2,5-dimethylphenoxymethyl)benzaldehyde, 2-(2,5-diethylphenoxymethyl)benzaldehyde, 2-(2,5-diisopropylphenoxymethyl)benzaldehyde, 2-(2,4,5-trimethylphenoxymethyl)benzaldehyde, 2-(2,4,6-trimethylphenoxymethyl)benzaldehyde, 2-(3,4,5-trimethylphenoxymethyl)benzaldehyde, 2-(2,5-dimethylphenoxymethyl)-3-chlorobenzaldehyde, 2-(2,5-dimethylphenoxymethyl)-4-chlorobenzaldehyde, 2-(2,5-dimethylphenoxymethyl)-5-chlorobenzaldehyde, 2-(2,5-dimethylphenoxymethyl)-6-chlorobenzaldehyde, 2-(2,5-diethylphenoxymethyl)-3-chlorobenzaldehyde, 2-(2,5-diethylphenoxymethyl)-4-chlorobenzaldehyde, 2-(2,5-diethylphenoxymethyl)-5-chlorobenzaldehyde, 2-(2,5-diethylphenoxymethyl)-6-chlorobenzaldehyde, 2-(2,5-diisopropylphenoxymethyl)-3-chlorobenzaldehyde, 2-(2,5- diisopropylphenoxymethyl)-4-chlorobenzaldehyde, 2-(2,5-diisopropylphenoxymethyl)-5-chlorobenzaldehyde, 2-(2,5-diisopropylphenoxymethyl)-6-chlorobenzaldehyde, 2-(2,5-dimethylphenoxymethyl)-4-bromobenzaldehyde, 2-(2,5-diethylphenoxymethyl)-4-bromobenzaldehyde, 2-(2,5-diisopropylphenoxymethyl)-4-bromobenzaldehyde, 2-(2,5-dimethylphenoxymethyl)-4-iodobenzaldehyde, and the like.

EXAMPLES

The present invention will be explained in more detail below by way of examples.

Production Example 1

Production of 2-(2,5-dimethylphenoxymethyl)benzal chloride

A 500 mL flask was charged with 84.3 g (0.69 mol) of 2,5-dimethylphenol and 147.7 g (0.74 mol) of a 20 wt % aqueous sodium hydroxide solution, the temperature of the resulting mixture was elevated to 80° C., and the mixture was stirred at the same temperature for 3 hours, and then it was cooled to 60° C. Another 500 mL flask was charged with 125.7 g (0.60 mol) of 2-(chloromethyl)benzal chloride and 9.7 g (0.03 mol) of tetra-n-butylammonium bromide, and the temperature of a flask content was elevated to 60° C. While an inner temperature of the flask content is maintained at 60° C., the above mixture prepared from 2,5-dimethylphenol and 20 wt % aqueous sodium hydroxide was added thereto dropwise over 3 hours. After completion of addition, the resulting mixture was stirred for 5 hours while an inner temperature of the mixture was maintained at 60° C. The resulting reaction mixture was subjected to liquid separation treatment at 60° C. to obtain an organic layer. When the organic layer was analyzed by a high-performance liquid chromatography internal standard method, the content of 2-(2,5-dimethylphenoxymethyl)benzal chloride was 94.8% by weight.

Example 1

A 1000 mL flask was charged with 270.2 g (4.50 mol) of acetic acid, 108.3 g (1.32 mol) of sodium acetate, 13.0 g (0.72 mol) of water, 0.5 g (0.002 mol) of tetra-n-butylammonium bromide and 192.6 g of the organic layer obtained in Production Example 1 (a content of 2-(2,5-dimethylphenoxymethyl)benzal chloride: 94.8 wt %) at 60° C., and the resulting mixture was heated to 120° C. and stirred for 8 hours. Thereafter, the resulting mixture was cooled to 80° C., 325 g of water and 325 g of xylene were added to the mixture, and the mixture was subjected to liquid separation treatment at 60° C. Xylene was distilled off from the resulting organic layer by concentration under reduced pressure, and the residue was cooled to obtain 143.5 g of a solid. When the solid was analyzed by a high-performance liquid chromatography internal standard method, the content of 2-(2,5-dimethylphenoxymethyl)benzaldehyde was 81.3% by weight.

Yield: 80.9% (based on 2-(2,5-dimethylphenoxymethyl)benzal chloride)

INDUSTRIAL APPLICABILITY

It has been known that 2-(aryloxymethyl)benzaldehyde compounds such as 2-(2,5-dimethylphenoxymethyl)benzaldehyde are useful as an intermediate for producing agricultural germicides. The present invention can be industrially utilized as a process for producing a 2-(aryloxymethyl)benzaldehyde compound.

The invention claimed is:

1. A process for producing a 2-(aryloxymethyl)benzaldehyde compound represented by formula (2):

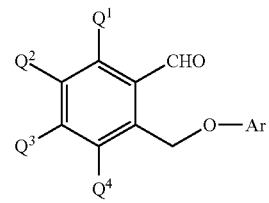

(2)

wherein $Q^1$, $Q^2$, $Q^3$ and $Q^4$ each represent independently a hydrogen atom or a halogen atom, and Ar represents a phenyl group optionally having a substituent, the process comprising a step of hydrolyzing a compound represented by formula (1):

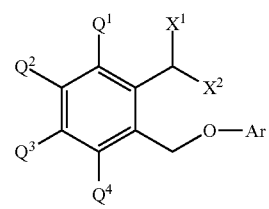

(1)

wherein $X^1$ and $X^2$ each represent independently a chlorine atom, a bromine atom or an iodine atom, and $Q^1$, $Q^2$, $Q^3$, $Q^4$ and Ar are each as described above, in the presence of an organic acid and a salt of an organic acid.

2. The process according to claim 1, wherein the step is a step of hydrolyzing the compound represented by formula (1) further in the presence of a phase transfer catalyst.

3. The process according to claim 1 or 2, wherein the organic acid is a carboxylic acid having 2 to 6 carbon atoms and the salt of an organic acid is an alkali metal salt of carboxylic acid having 2 to 6 carbon atoms.

* * * * *